United States Patent
Davis et al.

(10) Patent No.: US 10,350,307 B2
(45) Date of Patent: Jul. 16, 2019

(54) IN VIVO RNA OR PROTEIN EXPRESSION USING DOUBLE-STRANDED CONCATEMERIC DNA INCLUDING PHOSPHOROTHIOATED NUCLEOTIDES

(71) Applicant: General Electric Company, Schenectady, NY (US)

(72) Inventors: Brian Michael Davis, Niskayuna, NY (US); John Richard Nelson, Clifton park, NY (US); Wei Gao, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 18 days.

(21) Appl. No.: 15/707,074

(22) Filed: Sep. 18, 2017

(65) Prior Publication Data
US 2019/0083655 A1    Mar. 21, 2019

(51) Int. Cl.
| | | |
|---|---|---|
| *A61K 48/00* | (2006.01) | |
| *C12N 15/63* | (2006.01) | |
| *C12N 15/67* | (2006.01) | |
| *C07H 21/02* | (2006.01) | |
| *C07H 21/04* | (2006.01) | |

(52) U.S. Cl.
CPC .......... *A61K 48/0066* (2013.01); *C12N 15/63* (2013.01); *C12N 15/67* (2013.01); *C12Q 2531/125* (2013.01)

(58) Field of Classification Search
None
See application file for complete search history.

(56) References Cited

U.S. PATENT DOCUMENTS

| | | |
|---|---|---|
| 6,323,009 B1 | 11/2001 | Lasken et al. |
| 8,361,712 B2 | 1/2013 | Nelson et al. |
| 9,125,845 B2 | 9/2015 | Nelson et al. |
| 9,545,421 B2 | 1/2017 | Nelson et al. |
| 2008/0305142 A1 | 12/2008 | Chen et al. |
| 2010/0008939 A1 | 1/2010 | Nelson et al. |
| 2010/0055744 A1 | 3/2010 | Nelson et al. |
| 2016/0166710 A1* | 6/2016 | Baumhof ........... A61K 48/0075 514/44 R |
| 2016/0194368 A1* | 7/2016 | Hoge ..................... C12N 15/63 424/450 |
| 2019/0071704 A1* | 3/2019 | Nelson .................... C12P 21/00 |

OTHER PUBLICATIONS

Johne et al., "Rolling-Circle Amplification of Viral DNA Genomes using phi29 Polymerase", Trends in Microbiology, https://www.ncbi.nlm.nih.gov/pubmed/19375325, vol. 17, Issue 5, pp. 205-211, May 2009.

Stevens et al., "Multiply Primed Rolling-Circle Amplification Method for the Amplification of Circular DNA Viruses", Cold Spring Harbor Protocol, https://www.ncbi.nlm.nih.gov/pubmed/20360369, vol. 4, Apr. 2010.

Yata et al., "Efficient Amplification of Self-Gelling Polypod-like Structured DNA by Rolling Circle Amplification and Enzymatic Digestion", Scientific Reports, https://www.ncbi.nlm.nih.gov/pmc/articles/PMC4604513/, Oct. 2015.

\* cited by examiner

*Primary Examiner* — Sean McGarry
(74) *Attorney, Agent, or Firm* — Eversheds Sutherland (US) LLP

(57) ABSTRACT

A method for in vivo RNA or protein expression is provided. The method includes introducing a double-stranded concatemeric DNA into a eukaryotic cell to generate a desired RNA or protein. The double-stranded concatemeric DNA includes a plurality of tandem repeat sequences, wherein each of the plurality of tandem repeat sequences comprises an expression sequence. The double-stranded concatemeric DNA comprises one or more phosphorothioated nucleotides, wherein a ratio of phosphorothioated nucleotides to total nucleotides in the double-stranded concatemeric DNA is at least 1:1600. A eukaryotic cell comprising an exogenous, double-stranded concatemeric DNA comprising the plurality of tandem repeat sequences is also provided.

22 Claims, 4 Drawing Sheets

Specification includes a Sequence Listing.

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Lys Asp Asp Asp Asp Lys
1               5
```

IN VIVO RNA OR PROTEIN EXPRESSION USING DOUBLE-STRANDED CONCATEMERIC DNA INCLUDING PHOSPHOROTHIOATED NUCLEOTIDES

SEQUENCE LISTING

The instant application contains a Sequence Listing which has been filed electronically in ASCII format and is hereby incorporated by reference in its entirety. Said ASCII copy, created on Nov. 16, 2018, is named 319591-US-1_SL.txt and is 537 bytes in size.

FIELD OF INVENTION

The disclosure generally relates to RNA or protein expression systems that involve in vivo transcription and/or translation of a double-stranded concatemeric DNA. The disclosure particularly relates to in vivo RNA or protein expression using a double-stranded concatemeric DNA including phosphorothioated nucleotides.

BACKGROUND

Increase in various protein and RNA-based applications have increased the demand for large-scale production of RNA and protein. Most of these applications, especially therapeutic applications, require the protein/RNA to meet stringent quality criteria in terms of purity, potency, efficacy and safety. Recombinant protein production is often employed to meet the expectation of desired, large scale protein production. Higher production efficiencies and lower costs are much desired to make these protein/RNA products commercially viable.

Traditionally, for in vivo production of protein in mammalian cells, cell transfection using plasmid DNA has been used as a major tool. Production of a desirable protein or RNA from the corresponding DNA sequence involve use of large number of eukaryotic cells and is generally performed in large volume scales such as 100 L. For in vivo protein production, stable cell lines may be generated and expanded to adequate quantities to generate the desired protein yield. Further, in cases where the expressed protein is lethal to the host cells, a transient production system may be used. Significantly higher quantities of RNA or proteins may also be expressed in a shorter period using a cell-free, in vitro RNA or protein expression system. However, the in vitro transcription-translation system often requires larger quantities of a DNA template.

Generally, a plasmid DNA is used as a template DNA in in vivo and in vitro transcription-translation system. However, manufacturing of sufficient plasmid for transient/stable transfection or cell-free expression in larger scale is often expensive and cumbersome. For example, traditional methods of plasmid generation require labor-intensive cloning and plasmid purification. Further, traditional methods of large scale plasmid preparation run the risk of contamination by extraneous bacterial components and/or purification reagents, which may affect the downstream RNA expression and subsequent protein production.

A rapid, cost-effective production of suitable engineered DNA sequences, especially a DNA sequence containing only a promoter and a gene of interest, and devoid of any undesirable DNA sequences that are necessary for maintenance in a bacterium (e.g., origin of replication or an antibiotic resistance gene), which can be used for transfection in eukaryotic cells for subsequent RNA and/or protein production is highly desirable. Isothermal DNA amplification techniques such as rolling circle amplification (RCA) may be employed to generate such large quantities of high-quality DNA with less effort, time, and expense, starting from a circular nucleic acid template. For example, RCA enables rapid production of suitable engineered DNA sequences, for example, a DNA sequence containing only a promoter and a gene of interest.

Though few RNA and protein expression systems using eukaryotic cell lines and the RCA product DNA are currently available, however, those systems suffer from a rather low expression rate of the desired protein, resulting in low yields and high costs of the recombinant protein. There exists a need for an appropriate in vivo RNA and/or protein expression system that provide significant improvements in production of RNA and/or protein that are commercially viable.

BRIEF DESCRIPTION

In some embodiments, a method for in vivo RNA or protein expression is provided. The method comprises introducing a double-stranded concatemeric DNA into a eukaryotic cell to generate a desired RNA or protein. The double-stranded concatemeric DNA comprises a plurality of tandem repeat sequences, wherein each of the plurality of tandem repeat sequences comprises an expression sequence. The double-stranded concatemeric DNA comprises one or more phosphorothioated nucleotides, wherein a ratio of phosphorothioated nucleotides to total nucleotides in the double-stranded concatemeric DNA is at least 1:1600.

In some embodiments, a eukaryotic cell comprising an exogeneous, double-stranded concatemeric DNA comprising a plurality of tandem repeat sequences is provided. Each of the plurality of tandem repeat sequences comprises a phosphorothioated nucleotide, wherein a ratio of phosphorothioated nucleotides to total nucleotides is at least 1:1600.

DRAWINGS

These and other features, aspects and advantages of the invention will become better understood when the following detailed description is read with reference to the accompanying figures.

Figure 3:
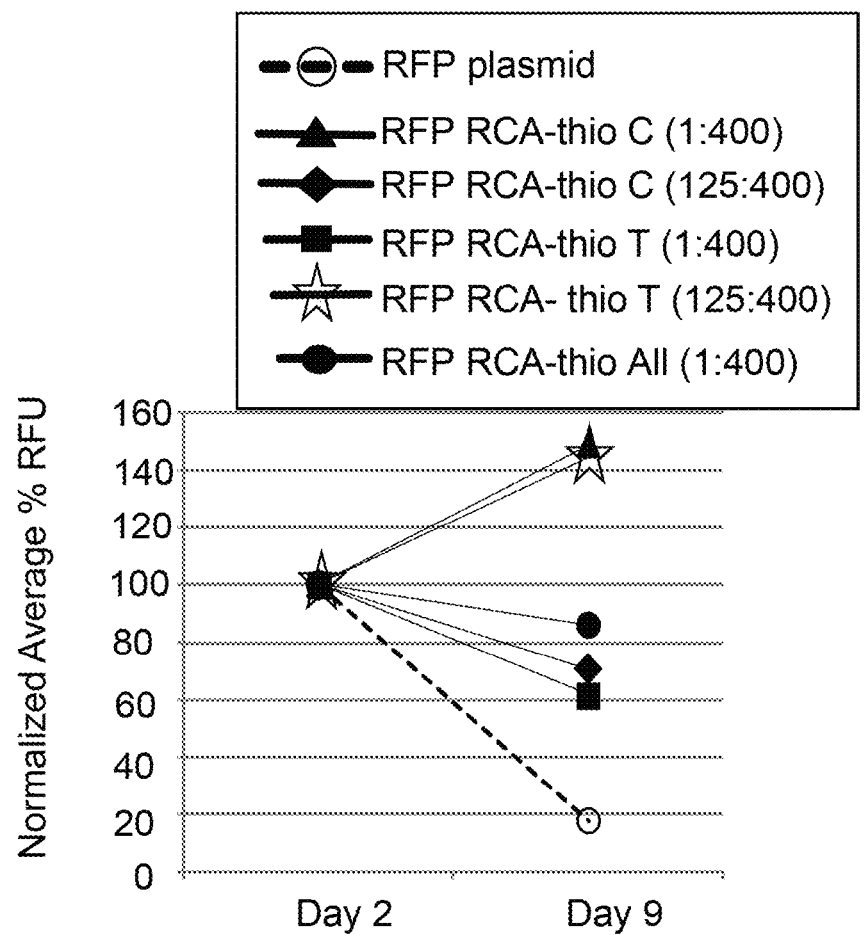

FIG. 3 illustrates in vivo expressions of red fluorescence proteins (RFP) after transfection of HEK293 cell with a RCA product DNA comprising phosphorothioated nucleotides, and a super coiled plasmid DNA at day 2 and day 9 post transfections, and indicates the in vivo stability of the RCA product DNA comprising phosphorothioated nucleotides (RCA-thio C, RCA-thio T or RCA-thio All) compared to super coiled plasmid DNA.

Figure 4:
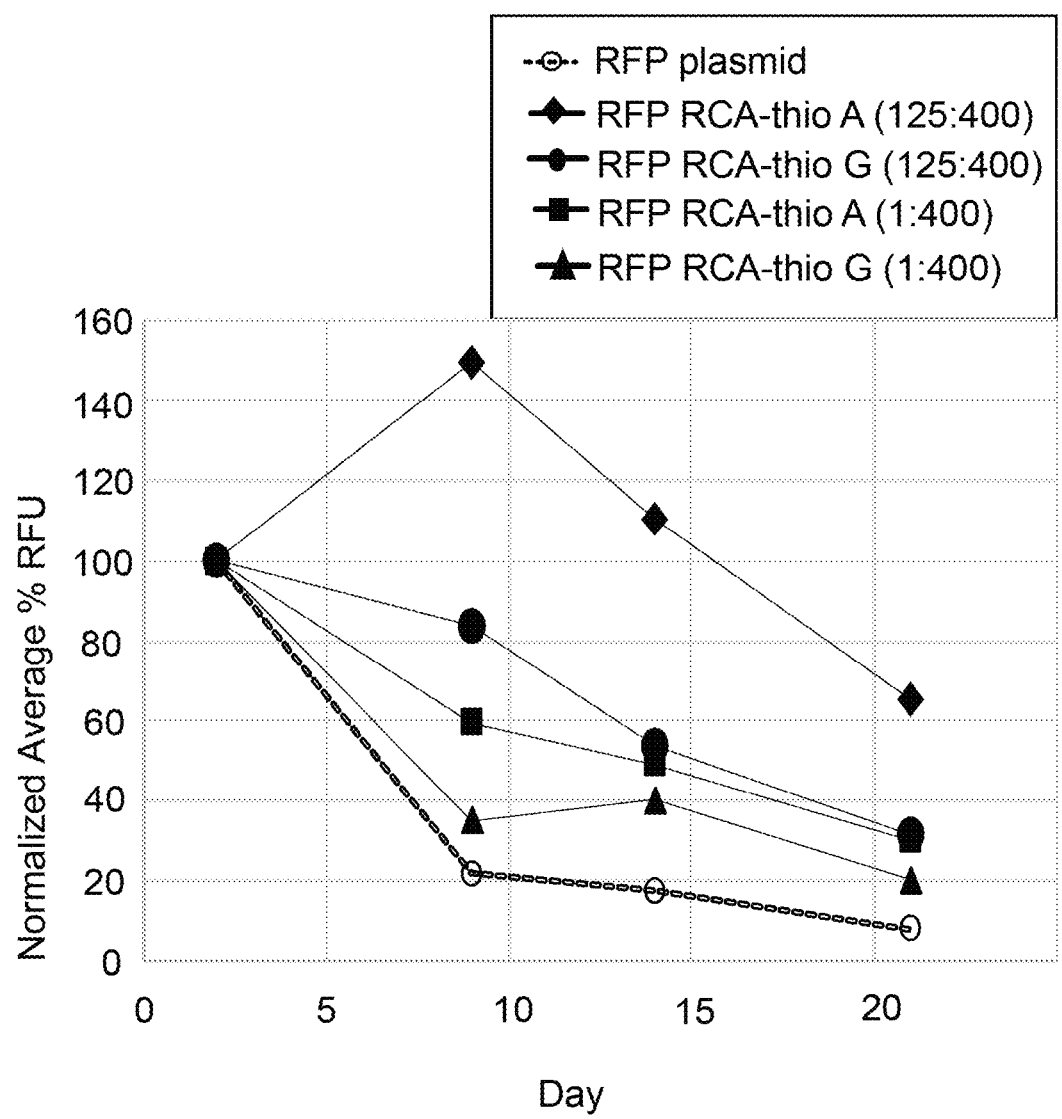

FIG. 4 illustrates in vivo expressions of red fluorescence proteins (RFP) after transfection of HEK293 cells with a RCA product DNA comprising phosphorothioated nucleotides (RCA thio-A or RCA thio-G) compared to super coiled plasmid DNA.

DETAILED DESCRIPTION

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Where necessary, ranges have been supplied and those ranges are inclusive of all sub-ranges there between. To more clearly and concisely describe and point out the subject matter of the claimed invention, the following definitions are provided for specific terms, which are used in the following description and the appended claims.

As used herein, the term "phosphorothioated nucleotide" refers to a nucleotide that has an altered phosphate backbone, wherein, the sugar moieties are linked by a phosphorothioate bond. In the phosphate backbone of an oligonucleotide sequence, the phosphorothioate bond contains a sulfur atom as a substitute for a non-bridging oxygen atom. This modification renders the internucleotide linkage resistant to nuclease degradation.

As used herein, the term "double stranded concatemeric DNA" refers to a double stranded DNA molecule that contains multiple copies of the same DNA sequences linked in series.

As used herein, the term "rolling circle amplification (RCA) product DNA" refers to a nucleic acid amplification product wherein a circular nucleic acid template (e.g., single/double stranded DNA circles) amplifies via a rolling circle amplification reaction mechanism. The rolling circle amplification typically produces concatamers comprising tandem repeat units of the circular nucleic acid template sequence. The rolling circle amplification product DNA may be generated by a linear RCA (LRCA), exhibiting linear amplification kinetics (e.g., RCA using a single, specific primer), or by an exponential RCA (ERCA) exhibiting exponential amplification kinetics. Rolling circle amplification product DNA may also be generated by using multiple primers (multiply primed rolling circle amplification or MPRCA), wherein the rolling circle amplification product DNA is hyper-branched concatamers. In a double-primed RCA, one primer may be complementary, as in the linear RCA, to the circular nucleic acid template, whereas the other may be complementary to the tandem repeat unit nucleic acid sequences of the RCA product DNA. The RCA product DNA may be generated by the RCA in vitro under isothermal conditions using a suitable nucleic acid polymerase such as Phi29 DNA polymerase.

As used herein the term "expression sequence" refers to a DNA sequence that is competent for RNA and/or protein expression. In embodiments, wherein protein expression is sought, the expression sequence is an expression competent unit that includes at least one promoter operably linked to one or more open reading frames (ORF). The one or more ORFs may code for one or more same or different proteins. In some instances, an expression sequence may include one promoter operably linked to more than one ORFs. For example, an expression sequence may include a promoter functionally linked to two different ORFs, one encoding a heavy chain, and the other encoding a light chain of an antibody. An expression sequence may further include sequences such as cap-independent translation element (CITE) for aiding efficient protein expression. In embodiments, wherein RNA expression is sought, the expression sequence is an RNA expression competent unit that includes at least one promoter and a transcription termination sequence.

One or more embodiments are directed to methods for generating a desired RNA or protein in eukaryotic cells by an in vivo expression (in vivo transcription and translation) system using a double-stranded concatemeric DNA. The double-stranded concatemeric DNA includes a plurality of tandem repeat sequences, and each of the plurality of tandem repeat sequences comprises an expression sequence. The double-stranded concatemeric DNA comprises one or more phosphorothioated nucleotides. The ratio of phosphorothioated nucleotides to total nucleotides in the double-stranded concatemeric DNA is at least 1:1600.

In vivo protein expression generally encompasses transcription of DNA to generate mRNA, and the simultaneous translation of mRNA to express protein in cells. In some embodiments, a RNA is generated by in vivo transcription of the double-stranded concatemeric DNA. In some embodiments, a protein is expressed by in vivo transcription and translation of the double-stranded concatemeric DNA. In some embodiments, the double stranded concatemeric DNA is a RCA product DNA. The RCA product DNA may further comprise additional nucleotide analogues, a modified nucleotide, or a combination thereof. The additional nucleotide analogue may have an altered phosphate backbone, sugar moiety, nucleobase, or combinations thereof. For example, additional nucleotide analogue may be a Locked Nucleic Acid (LNA) nucleotide, or a Peptide Nucleic Acid (PNA). As used herein, the term "modified nucleotides" refers to nucleotides wherein an additional moiety is attached the nucleotides (e.g., a biotinylated nucleotide). These in vivo transcription and/or translation reactions provide higher expression of RNA and/or protein. The double-stranded concatemeric DNA containing phosphorothioated nucleotides provides enhanced nuclease resistance property.

In some embodiments, multiple (e.g., two or more) separate double stranded concatemeric DNA may be employed for in vivo protein expression, wherein each of the separate double stranded concatemeric DNA includes expression sequences encoding different proteins. For example, two RCA product DNAs may be employed, wherein a first RCA product DNA includes a first expression sequence encoding a first protein, and a second RCA product DNA includes a second expression sequence encoding a second protein, wherein the first protein is different from the second protein.

In some embodiments, at least one sequence of the tandem repeat sequences of the double-stranded concatemeric DNA includes one or more phosphorothioated nucleotides. In some embodiments, each of the tandem repeat sequences of the double stranded concatemeric DNA comprises one or more phosphorothioated nucleotide. The phosphorothioated nucleotides are incorporated in RCA product DNA by using phosphorothioated dNTPs such as α-S-dATP and α-S-dTTP in RCA reaction. The term "phosphorothioated" nucleotide is interchangeably used hereinafter as a "thioated" nucleotide. The term "total nucleotides" refers to the total number of thioated nucleotides and non-thioated nucleotides in particular nucleic acid sequence. The thioated nucleotides may be incorporated by using one or more thioated dNTPs in a DNA amplification reaction that is used to produce the double-stranded concatemeric DNA. For example, in a DNA amplification reaction, at least a portion of dATP may be substituted with thioated dATP. In some other embodiments, a combination of thioated dATP, dGTP, dCTP, and/or dTTP may be used in the DNA amplification reaction that is used for the generation of the double-stranded concatemeric DNA. A thioated dNTP, such as α-S-dATP is added in a pool of non-thioated dNTP mixture, such as a mixture of dATP, dGTP, dTTP and dCTP. A ratio of thioated dNTP to total dNTP (including thioated and non-thioated dNTPs) is calculated by dividing a concentration of thioated nucleotide added to a reaction mixture containing a mixture of thioated and non-thioated dNTPs by a concentration of the total nucleotides (thioated and non-thioated).

In some embodiments, the double-stranded concatemeric DNA is an RCA product DNA that is generated by rolling circle amplification. The RCA product DNA may be a linear or a branched concatamer. In some embodiments, each of the tandem repeat sequences comprises phosphorothioated nucleotides. The RCA product DNA including phosphorothioated nucleotide exhibits increased stability towards restriction digestion in comparison with an RCA product DNA that does not contain any phosphorothioated nucleotide or with a super coiled plasmid DNA (see, for example, FIG. 1, Example 2 that clearly demonstrates that a thioated RCA product DNA is resistant to exonuclease activity). The thioated RCA product DNA (lanes 7-9 of FIG. 1) showed higher stability compared to the RCA product DNA that does not contain any phosphorothioated nucleotide (lanes 4-6 of FIG. 1) or super coiled plasmid DNA (lanes 1-3 of FIG. 1). As noted, "thioated RCA product DNA" refers to the RCA product DNA comprising at least one phosphorothioated nucleotide. Further, the "non-thioated RCA product DNA" refers to a RCA product DNA which does not contain any phosphorothioated nucleotide.

In some embodiments, the ratio of phosphorothioated nucleotides to total nucleotides in the double-stranded concatemeric DNA is in a range of 1:1600 (i.e., 0.001) to 125:1600 (i.e., 0.078). In some other embodiments, the ratio of phosphorothioated nucleotides to total nucleotides in the double-stranded concatemeric DNA is in a range of 50:1600 (or 0.031) to 125:1600 (or 0.078). In certain embodiments, the ratio of phosphorothioated nucleotides to total nucleotides in the double-stranded concatemeric DNA is in a range of 75:1600 (or 0.047) to 125:1600 (or 0.078). In one or more embodiments, the ratio of phosphorothioated nucleotides to total nucleotides in the double-stranded concatemeric DNA is 125:1600 (or 0.078). In some embodiments, the ratio of phosphorothioated nucleotides to total nucleotides in the double-stranded concatemeric DNA is 1:40 (i.e., 0.025). In certain embodiments, the ratio of phosphorothioated nucleotides to total nucleotides in the double-stranded concatemeric DNA is 1:16 (i.e., 0.062). In one alternate embodiment, the ratio of phosphorothioated nucleotides to total nucleotides in the double-stranded concatemeric DNA is 1:1. In such embodiments, double-stranded concatemeric DNA include equal numbers of thioated and non-thioated nucleotides. In some embodiments, all the nucleotides of the double-stranded concatemeric DNA, such as RCA product DNA, are phosphorothioated. In other words, the double-stranded concatemeric DNA contains 100% phosphorothioated nucleotides.

Figure 2:
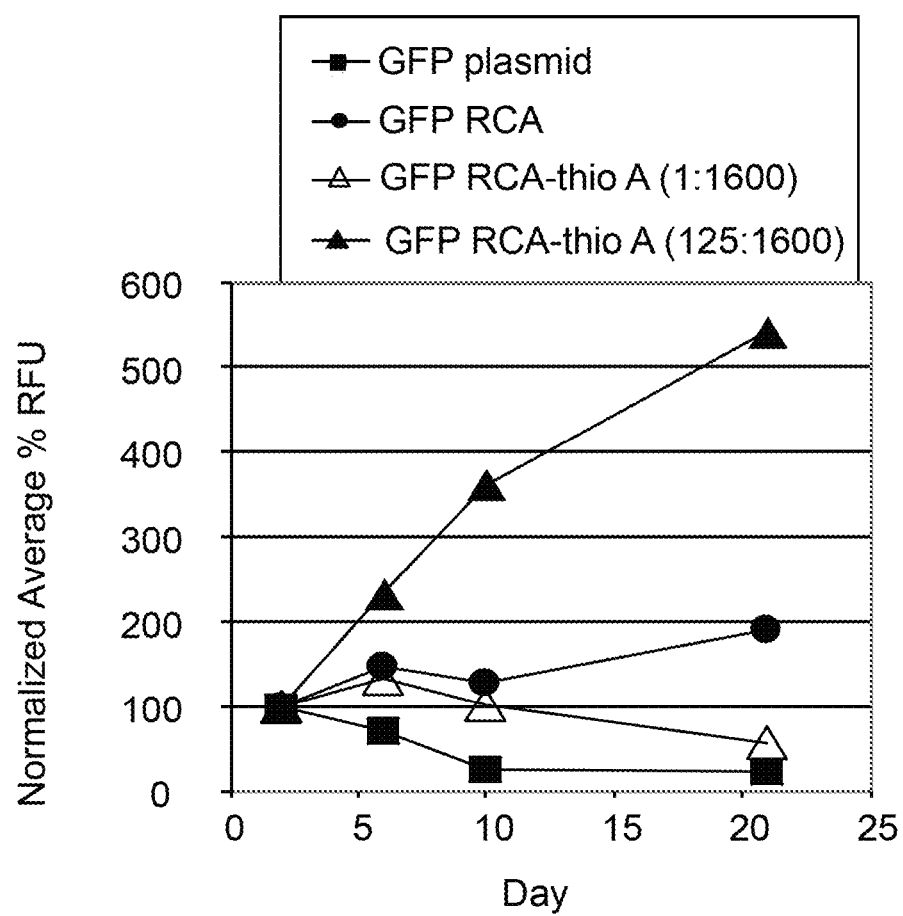
FIG. 2 illustrates in vivo expressions of green fluorescence proteins (GFP) after transfection of HEK293 cell with a RCA product DNA comprising phosphorothioated nucleotides, a RCA product DNA devoid of phosphorothioated nucleotides, and a super coiled plasmid DNA. Signal is normalized to the relative fluorescence units determined on day 2.

The enhanced yield of GFP (FIG. 2) and RFP (FIGS. 3-4) are shown using thioated RCA product DNA compared to super coiled plasmid DNA and non-thioated RCA product DNA. Protein yields employing thioated RCA product DNA (e.g., 1:1600, 125:1600) were higher than that of non-thioated RCA product DNA and supercoiled plasmid DNA, which is described in detail in Examples 3 and 4 and depicted in FIGS. 2-4. In these examples, in vivo protein expressions for GFP and RFP were enhanced when a thioated RCA product DNA generated from plasmid pAcGFP1-Hyg-C1 DNA encoding GFP or plasmid pCMV6-AC-mKate DNA encoding RFP) was expressed compared to non-thioated RCA product DNA (generated from the same plasmid DNAs) and supercoiled plasmid DNA (FIGS. 2-4). Further, RCA product DNA showed higher in vivo stability compared to super coiled plasmid DNA, as shown in FIGS. 2-4. For example, FIG. 2 illustrates increased in vivo stability of thioated RCA product DNA compared to the supercoiled plasmid DNA and non-thioated RCA product DNA after transfection into the HEK293 cells by expression of green fluorescence protein (GFP). FIG. 2 showed that thioated and non-thioated RCA product DNA remain intact for a greater duration of time (e.g., 20 days) during in vivo protein expression compared to supercoiled plasmid DNA. However, thioated RCA DNA showed maximum stability and activity even after 20 days of transfection to HEK293 cells. FIGS. 3-4 illustrate increased in vivo stability of thioated RCA product DNA compared to the supercoiled plasmid DNA after transfection into the HEK293 cells by expression of red fluorescence protein (RFP). The FIGS. 2-4 also indicate the increased stability and higher protein expression with increasing amount of phosphorothioated nucleotides in the RCA product DNA. For example, thioated RCA product DNA with 125:1600 showed higher stability and enhanced protein expression compared to 1:1600.

In some embodiments, the double-stranded RCA product DNA that is used for in vivo protein expression comprises thioated nucleotides. The RCA product DNA having phosphorothiated nucleotides is produced by rolling circle amplification. In these embodiments, the RCA reactions are supplemented with thioated dNTPs, such as α-S-dATP or α-S-dTTP, into the dNTP mixture for random incorporation of thioated bases into the RCA product DNA while amplification. Protein expression is improved when an RCA product comprising thioated nucleotides is used for in vivo transcription and translation when compared to non-thioated RCA products. In some embodiments, the double-stranded concatemeric DNA, such as an RCA product DNA, may be internally thioated (have α-S-dNTP). In such embodiments, to generate a double-stranded concatemeric DNA that are internally thioated, RCA reactions are supplemented with phosphorothioated nucleotides. The phosphorothioated nucleotides are incorporated into the dNTP mixture for random incorporation of thioated bases into the RCA product DNA during amplification. In some other embodiments, a double-stranded concatemeric DNA, such as an RCA product DNA comprising a phosphorothioated nucleotide may be generated (e.g., thioated, having α-S-dNTP) by employing a thioated primer sequence for the RCA reaction.

The RCA product DNA used for in vivo RNA or protein expression may be processed DNA or unprocessed DNA.

The "processing" of the RCA product DNA may include an act of restriction digestion, chemical denaturation, heat denaturation, self-cleaving, or enzymatically cleaving of the RCA product DNA of interest. The "processing" of the RCA product DNA may also include purification of the RCA product DNA of interest. In some embodiments, the RCA product DNA can be employed as a DNA template for in vivo protein expression without any purification. In some embodiments, the double-stranded concatemeric DNA may be processed to form linear, or circular DNA template for transfection. The linear concatemeric DNA may be inserted into a plasmid vector before transfecting into the eukaryotic cells. In such embodiments, the linear concatemeric DNA may be subjected to restriction digestion to produce fragmented DNA followed by inserting the fragmented DNA into a plasmid vector using recombination technology. In addition, the linear concatemeric DNA may be treated with a recombinase or pro-telomerase or other enzymes to generate circularized, fragmented DNA. In some embodiments, the RCA product DNA is transfected or introduced into the eukaryotic cells without any further processing. In such embodiments, the RCA product is not subjected to any kind of restriction digestion or self-cleaving to form smaller fragments before using it as a DNA template for in vivo protein expression. In some other embodiments, the RCA product is not subjected to any chemical denaturation or heat denaturation to denature the RCA product DNA before employing the DNA template for introducing into the eukaryotic cells for in vivo protein expression. However, in some embodiments, the RCA product DNA may be separated (e.g., by precipitation) to remove salts or any other contaminants, such as primers or smaller fragmented DNA from the reaction medium before proceeding for transfection.

The RCA product DNA generated by rolling-circle amplification reaction often, which employs reagents such as a primer, a nucleic acid polymerase, and free nucleotides (dNTPs). The nucleic acid polymerase may be a proofreading nucleic acid polymerase, including, but not limited to, a Phi29 DNA polymerase. In some embodiments, the reagents used in the RCA may be pre-treated e.g., by ultraviolet radiation or de-contaminated by incubating the reagents in presence of a nuclease and its co-factor. During the amplification reaction, the DNA template is replicated by a polymerase in the presence of dNTPs (for example, dATP, dGTP, dCTP or dTTP), modified dNTPs (e.g. thioated dNTPs, such as α-S-dGTP, α-S-dCTP, α-S-dATP, and α-S-dTTP), or combinations thereof. RCA may be performed using commercially available RCA amplification kits such as Illustra™ TempliPhi™ Amplification Kit (GE Healthcare Life Sciences).

The RCA reaction may be performed using a random primer mixture or specific primers. Primer sequences comprising one or more nucleotide analogues may also be used. For example, the nucleotide analogues may include phosphorothioated nucleotide, an inosine, a Locked Nucleic Acid (LNA) nucleotide, a Peptide Nucleic Acid (PNA) nucleotide, 2-amino-deoxyadenosine, 2-thio-deoxythymidine, a polycation nucleotide, Zip Nucleic Acid (ZNA) polycation modified nucleotide, or combinations thereof. In one or more embodiments, the random primer mixture has nuclease-resistant primers (e.g., primer sequences comprising phosphorothioate groups at appropriate positions), random hexamers or a hexamer primer.

In some embodiments, the RCA product DNA is generated by using an RCA reaction having a final concentration of dNTPs in a range of about 10 μM to about 10 mM. In one or more embodiments of RCA reactions, the dNTP concentration is less than 10 mM. In these embodiments, the concentration of dNTPs is kept lower than 10 mM to avoid hydrogel formation from the RCA product and to remain at a concentration below or equal to the amount of divalent cation (e.g. magnesium) present in the reaction buffer. Hydrogel formation may occur after amplification in the presence of a high concentration of dNTPs which may further complicate the downstream manipulation such as pipetting and processing of the RCA product. Hydrogel formation may be observed when dNTP concentration of 50 mM or more is used in the RCA reaction.

The expression sequence in each of the plurality of tandem repeat sequences may comprise a coding sequence, a non-coding sequence, or a combination thereof. In some embodiments, the expression sequence further comprises a polyA sequence, a translational enhancer sequence, a transcriptional termination sequence, a ribosomal binding site, a translational termination sequence, an insulator sequence, or combinations thereof. The expression sequence may further include a pre-promoter sequence, a sequence for protease cleavage or nucleotide cleavage, a sequence for protein purification, or combinations thereof.

In some embodiments, the expression sequence contains a coding sequence, wherein the coding sequence generates a desired protein in the eukaryotic cell. The coding sequence is a nucleic acid sequence containing a particular gene of interest. In general, the coding sequence comprises a promoter, and an open reading frame (ORF). The coding sequence may optionally include a cap-independent translation element (CITE). In some embodiments, the coding sequence further comprises a ribosomal binding site. The coding sequence may comprise a transcription terminator sequence located outside the open reading frame but within the expression sequence. In one or more embodiments, the open reading frame of the coding sequence comprises a codon-optimized sequence, a purification tag sequence, a protease cleavage site or combinations thereof. In some embodiments, the expression sequence comprises both coding and non-coding sequences.

In one or more embodiments, each of the plurality of tandem repeat sequences comprises at least one expression sequence. In some embodiments, the at least one expression sequence comprises at least one coding sequence. In such embodiments, the at least one coding sequence of the at least one expression sequence comprises at least one promoter, and at least one open reading frame. In some embodiments, each of the plurality of tandem repeat sequences comprises two or more expression sequences. The two or more expression sequences including coding sequences may code for a same protein or different proteins. In some embodiments, the expression sequence includes at least one promoter that is functionally linked to at least one open reading frame. For example, in one aspect, in an expression sequence, one promoter is functionally linked to one open reading frame. In another aspect, in an expression sequence, one promoter is functionally linked to two different open reading frames. In some embodiments, the expression sequence may include two or more promoters functionally linked to two or more open reading frames.

An expression sequence may include a promoter operably linked to two different open reading frames, such as a first open reading frame and a second open reading frame, each of them coding a protein that is different from the other. In this example, a single promoter is functionally linked to two open reading frames via a cap-independent translation element. Each of the open reading frames includes translation start and translation stop sequences. A translational termination or stop sequence is required for an expression sequence, otherwise an infinite polyprotein may be synthesized, which is undesirable. However, a transcriptional stop codon may be optional for the first open reading frame leading to the generation of a polycistronic mRNA upon transcription. In such instances, the intervening sequences between the first and second open reading frames may be selected such that upon in vivo protein expression, even if a single polycistronic mRNA is produced, it can be translated to two different proteins. Synthesis of the first protein by translation of the first open reading frame may be followed by a ribosomal slippage to the second translation start sequence of the second open reading frame to initiate the synthesis of the second protein from the second open reading frame. This may be achieved by incorporating "self-cleaving sequences" between the first and second open reading frames. Suitable self-cleaving sequences such as viral P2A motif facilitates the creation of two or more proteins from one single mRNA.

In some embodiments, the expression sequence contains a non-coding sequence, wherein the non-coding sequence generates a desired RNA. Such expression sequence does not contain any coding sequence. The non-coding sequence comprises a promoter and a transcription termination sequence. The non-coding sequence is generally devoid of an open reading frame. The expression sequence that contains a non-coding sequence is also referred to as an RNA expression sequence. In some embodiments, the expression sequence consists essentially of a noncoding sequence. In some other embodiments, the expression sequence includes both the coding and non-coding sequences, wherein the RNA can be generated from a non-coding sequence of an expression sequence. In such embodiments, a desired protein may also be subsequently generated from the coding sequence of the same expression sequence. In some embodiments, the generated RNA may be extracted from the eukaryotic cells for different downstream applications. In one embodiment, the extracted RNA may subsequently be packaged into a lentivirus system to deliver in another cell. The non-coding sequence may include, but is not limited to, a sequence for antisense RNA, a short interfering RNA (siRNA), a short hairpin RNA (shRNA), a microRNA (miRNA), a microRNA mimic, a transfer RNA (tRNA), a ribosomal RNA (rRNA), or combinations thereof. The non-coding sequence may also include CRISPR RNAs (tracrRNA, crRNA, sgRNA, or gRNA), small nuclear RNA (snRNA), small nucleolar RNA (snoRNA), Piwi interacting RNA (piRNA), telomerase RNA, spliceosome RNA, enhancer RNA, retrotransposons, X inactive specific transcript (Xist), RNAs encoded by RNA polymerase I and RNA polymerase III, or combinations thereof.

As noted, both the coding sequence and the non-coding sequence comprise a promoter. Any of the suitable promoters known in the art, including, for example, T7 RNA polymerase or CMV promoter sequences, may be used in the methods described herein. Likewise, any of suitable ribosomal binding sites known in the art, including but not limited to, IRES, polyA tracts, species-independent translational leaders (SITS), Kozak consensus sequences, and Shine-Dalgarno sequences may be used.

The open reading frame includes translation start and translation stop sequences. In some embodiments, the open reading frame comprises a codon-optimized sequence for enhancing translation. The open reading frame may comprise an amino-terminal peptide fusion sequence derived from an internal ribosome entry site (IRES) for enhanced ribosome recognition, a tag sequence for purification of the desired protein, or a combination thereof. The CITE may comprise an IRES, a translation enhancing element (TEE), or a combination thereof.

The desired protein may be purified by a tag sequence, wherein the tag sequence may be fusion tag for affinity purification, tag for protease cleavage or combinations thereof. The fusion tag for affinity purification may be used for rapid purification and detection of the expressed proteins. These tags are also referred as affinity tag. The affinity tag may include a polyhistidine tag, Glutathione S-transferase tag (GST), haemagglutinin (HA), myc (derived from c-myc gene product), FLAG (consisting of eight amino acids Asp-Tyr-Lys-Asp-Asp-Asp-Asp-Lys (SEQ ID NO: 1) including an enterokinase-cleavage site) or combinations thereof. The fusion tags help in rapid purification or detection of the desired protein, however, the tags may not be considered to be permanent fixtures or domains of the recombinant proteins. Hence, removal of the fusion tag is often needed for highly analytical studies of recombinant protein structure and function. The tag for purification may be removed from the protein by using another type of tag, such as protease cleavage tag. The protease cleavage tag may be used to cleave a distinct peptide bond within a specific protein or peptide sequence. The protease cleavage tag may include, for example, PreScission™ Protease tag (GE Healthcare Life Sciences) or thrombin protease tag (GE Healthcare Life Sciences).

As noted, the open reading frame of the coding sequence may comprise a codon-optimized sequence, wherein the codon optimized sequence is generated by considering different factors, such as codon bias, contextual codon preference, and/or individual codon preference. The codon-optimized sequence of the open reading frame may enhance the rate or quality of translation of the RCA product. Codon optimization generally improves the protein expression from the coding sequence by increasing the translational efficiency of a gene of interest. The functionality of a gene may also be increased by optimizing codon usage within the custom designed gene. In codon optimization embodiments, a codon of low frequency in a species may be replaced by a codon with high frequency, for example, a codon UUA of low frequency may be replaced by a codon CUG of high frequency for leucine. Codon optimization may increase mRNA stability and therefore modify the rate of protein translation or protein folding. Further, codon optimization may customize transcriptional and translational control, modify ribosome binding sites, or stabilize mRNA degradation sites.

The transcription termination sequence is generally situated at the 3' end of a gene in a DNA template. The transcription termination sequence provides signal in the newly synthesized mRNA to initiate the process of releasing the mRNA from the transcriptional complex, which can also aid in effective translation of the desired protein product. The insulator sequence generally enhances the efficiency of ribosomal binding or translational initiation. Numerous examples of suitable insulator sequences that exist in the art may be used, including for example, sequences encoding poly-histidine tracts. In some embodiments, the insulator sequence may be determined empirically by inserting spacer sequences around the ribosomal binding site or by optimizing or inserting codons within the N-terminus of the expressed protein.

In some embodiments, the expression sequence comprises a coding sequence, a non-coding sequence, or a combination thereof. The coding sequence comprises a promoter, an open reading frame, and optionally a cap-independent translation element (CITE). The cap-independent translation element (CITE) of the coding sequence may be an internal ribosome entry site (IRES), a translation enhancing element (TEE), or a combination thereof. The open reading frame of the coding sequence may be codon-optimized for enhancing translation. The open reading frame may further comprise a tag sequence for purification of the desired protein, an amino-terminal peptide fusion sequence derived from an IRES for enhanced ribosome recognition, or a combination thereof. The expression sequence further comprises a polyA sequence, a transcriptional termination sequence, an insulator sequence, or a combination thereof.

In some embodiments, the expression sequence is a minimalistic expression sequence that is devoid of any extraneous sequences that are required for propagation of a plasmid in a host cell. The minimalistic expression sequence for expressing a desired protein includes, at the minimum, a promoter, a ribosomal binding site, and a translational termination sequence. The minimalistic expression sequence for expressing a desired RNA includes, at the minimum, a promoter, a ribosomal binding site, and a translational termination sequence. In some embodiments, the double-stranded RCA product DNA consists essentially of tandem repeats of a minimalistic expression sequence. In such embodiments, the expression sequence may additionally contain sequences that do not materially affect the in vivo protein expression or RNA expression using the RCA product DNA as a template. For example, it may further include sequences such as a translational enhancer sequence, an insulator sequence, or a transcriptional termination sequence. The minimalistic expression sequence of the RCA product DNA excludes any extraneous sequences, such as antibiotic selection gene, or any other accessory sequences that are required for cloning, selection, screening and/or replication in a host cell. The RCA product may be a linear or a branched concatamer containing tandem repeats of the minimalistic expression sequence. The minimalistic expression sequence of the RCA product DNA may be derived from a DNA mini-circle that includes only minimalistic expression sequence.

The double-stranded concatemeric DNA may further comprise an inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide, or a combination thereof. In some embodiments, the modified nucleotides, such as inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide are part of a primer sequence that is employed for rolling circle amplification.

The double-stranded concatemeric DNA may be delivered to a eukaryotic cell by any method, including but not limited to, electroporation, sonoporation, impalefection, transduction, optical transfection, magnetofection, nucleofection, hydrodynamic delivery, heat shock-mediated gene delivery, nanoparticle mediated gene-gun delivery, calcium phosphate-mediated delivery, cationic polymer-mediated delivery, or liposome-mediated delivery.

In some embodiments, a eukaryotic cell comprising an exogeneous, double-stranded concatemeric DNA comprising a plurality of tandem repeat sequences is provided. Each of the plurality of tandem repeat sequences comprises a phosphorothioated nucleotide, wherein a ratio of phosphorothioated nucleotides to total nucleotides is at least 1:1600. The exogeneous, double-stranded concatemeric DNA employed for transfection into eukaryotic cells to generate the said cell may be an unprocessed or a processed RCA product DNA. The eukaryotic cell may be a protozoa, a yeast cell, an insect cell, or a mammalian cell.

A variety of methods may be used to prepare a DNA mini-circle template for use with methods of the invention. In some embodiments, a linear DNA template may be circularized to generate a DNA mini-circle template. In one example embodiment, the circularization of the linear DNA template may be effected by an enzymatic reaction, for example, by incubation with a ligation enzyme such as DNA ligase. In some embodiments, the terminal ends of the linear DNA template are hybridized to a nucleic acid sequence such that the terminal ends come in close proximity. Incubating with a ligation enzyme may then effect the circularization of the hybridized linear DNA template to generate a DNA mini-circle. Suitable DNA mini-circle template may also be generated by PCR amplification of a portion of a larger DNA (for example, a genomic DNA, or a DNA from a DNA library) using appropriate PCR primers, followed by circularization of the PCR product. DNA mini-circle may also be generated by chemical synthesis of suitable linear oligonucleotides followed by circularization of the synthesized oligonucleotide. In some embodiments, the synthesized linear oligonucleotides may consist essentially of minimalistic expression sequence and achieve circularization via DNA ligase to generate DNA mini-circle.

EXAMPLES

Unless specified otherwise, ingredients described in the examples are commercially available from common chemical suppliers. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

Materials: HEK293 cells were obtained from ATCC (catalog no. CRL-1573), DMEM, L-glutamine, and 1% Pen/Strep were obtained from Gibco (Thermo Fisher, Waltham, Mass., US). Tris buffer pH 8 was obtained from Ambion® (MA, US). 10% Fetal Bovine Serum (FBS) was purchased from Thermo Fisher Scientific (MA, USA). Lipofectamine 2000 (catalog no. 11668-027) was from Invitrogen (Thermo Fisher, Waltham, Mass., US). Hind III, ExoI and Exo III enzymes were purchased from New England Biolabs (Ipswich, Mass., USA). Typhoon variable-mode Imager was obtained from GE Healthcare (Piscataway, N.J., USA). Microfuge tubes and 96-well cell culture plate were obtained from Fisher Scientific (Hampton, N.H., US). dNTPs and random hexamer primers were obtained from GE Healthcare Life Sciences (Piscataway, N.J., USA) and Sp isomer of alpha-thio-dNTPs (such as Sp-dTTPαS, Sp-dGTPαS, Sp-dATPαS, and Sp-dCTPαS) were obtained from Biolog—Life Science Institute (Bremen, Germany). Phi29 DNA polymerase (1 mg/ml) was from Enzymatics (Beverly, Mass., USA). Oligonucleotides (such as primers for RCA) were purchased from Integrated DNA Technologies (IDT Inc, Iowa, USA). Hanks' Balanced Salt Solution (HBSS), HEPES were purchased from HyClone, GE Healthcare (Utah, US).

Plasmid vectors pAcGFP1-Hyg-C1, and pCMV6-AC-mKate were from Clontech Laboratories (Mountain View, Calif., US). The plasmid vectors were used as received without any modification to the vector sequence. Plasmid map and sequence for each of the vectors are available from the respective vendors.

Plasmid RW218 was generated by inserting the codon-optimized H1 hemagglutinin (HA) gene into an expression cassette that uses the human cytomegalovirus immediate early promoter. Additional sequences were included to improve expression, specifically the HBV pre-S2 5' UTR, CMV exon ½ (consisting of the first two CMV IE exons spliced together by deletion of the natural intron), rat insulin intron A, HBV env enhancer, and rabbit beta globin poly A (rGpA). The HA coding sequence (Peter T. Loudon, Eric J. Yager, Debbie T. Lynch, Amithi Narendran, Cristy Stagnar, Anthony M. Franchini, James T. Fuller, Phil A. White, Julia Nyuandi, Clayton A. Wiley, Michael Murphey-Corb, and Deborah H. Fuller, "GM-CSF Increases Mucosal and Systemic Immunogenicity of an H1N1 Influenza DNA Vaccine Administered into the Epidermis of Non-Human Primates", PLoS One. 2010; 5(6): e11021.) was synthesized at GeneArt (Regensburg, Germany) from the full-length amino acid sequence of the influenza A/New Caledonia/20/99 (H1N1) hemagglutinin protein obtained from the Influenza Sequence Database (Macken, C., Lu, H., Goodman, J., & Boykin, L., "The value of a database in surveillance and vaccine selection." In Options for the Control of Influenza IV. A. D. M. E. Osterhaus, N. Cox & A. W. Hampson (Eds.) Amsterdam: Elsevier Science, 2001, 103-106.), using a codon usage pattern commonly found in human genes (Kazusa Genome Database, Kazusa DNA Res. Inst.).

10 mM Tris, pH 8.0 was prepared from a stock of 1 M Tris, pH 8 (Ambion®, MA, US). A complete medium containing DMEM, 10% Fetal Bovine Serum (FBS) and 2 mM L-Glutamine was used for culturing cells. For flow cytometry, a medium comprising Hanks' Balanced Salt Solution (HBSS) with 20 mM HEPES, pH 8, 16.8 mM D-glucose, and 10% FBS was used. The Sp-isomers of dNTP and dNTP mixture used for preparing RCA product DNA was 1:1600 and 125:1600 ratio.

Example 1: Generation of RCA Product DNA

The RCA product DNA was generated from a supercoiled plasmid DNA template (e.g., pAcGFP1-Hyg-C1, pCMV-AC-mKate2) by an RCA reaction. The plasmid RW218 was used as a control.

Rolling Circle Amplification (RCA) of Plasmid DNA

Preparation of reagents: RCA reagents, including water, reaction buffer, primers, and phi29 enzyme were pre-cleaned prior to the addition of template DNA and dNTPs to minimize off-target amplification. The primer-nucleotide solution (primer-nucleotide mix) containing an exonuclease-resistant primer and the nucleotides (dNTPs) was decontaminated by incubating the primer-nucleotide mix with a combination of exonuclease I, exonuclease III, and a single stranded DNA binding protein (SSB protein). The enzyme mix containing a DNA polymerase was decontaminated by incubating with a divalent cation (e.g., $Mg^{2+}$) optionally in presence of an exonuclease.

Primers for generating RCA product: The amplification of the plasmid DNA template for generating RCA product DNA was performed using random hexamers NNNN*N*N for pAcGFP1-Hyg-C1 or hexamer primers having the sequence W+W+N*N*S for pCMV-AC-mKate2, where "N" represents a random nucleotide (i.e., N may be any of A, C, G, or T/U), "at N" represents any of 2-amino dA, 2-thio dT, normal G or normal C, a plus (+) sign preceding a letter designation denotes that the nucleotide designated by the letter is a locked nucleic acid (LNA) nucleotide, and a star (*) sign preceding a letter denotes that the nucleotide designated by the letter is a phosphorothioated modified nucleotide.

dNTPs and modified dNTPs: RCA product DNA was synthesized using a complete set of traditional dNTPs, or by using mixtures of traditional dNTPs and Sp isomer of alpha-thio-dNTPs (such as Sp-dTTPαS, Sp-dGTPαS, Sp-dATPαS, and Sp-dCTPαS). The Sp isomer of alpha-thio-dNTPs is interchangeably used herein as α-S-dNTPs. For example, a 1:1600 ratio of Sp-ATPαS to total dNTP mixture containing Sp-ATPαS and non-thioated traditional dNTP was used in one amplification. For all RCA reactions, the dNTP concentration was maintained below 1 mM (typically 400-800 µM) to avoid hydrogel formation of the amplified RCA product DNA, which can potentially complicate the downstream usability of the RCA product DNA.

Plasmid DNA Template: pAcGFP1-Hyg-C1 plasmid containing an insert of the GFP gene was used for expressing GFP, plasmid pCMV-AC-mKate containing an insert of the RFP gene was used for expressing RFP, and plasmid RW218 containing an insert of the HA gene was used as negative control. Ten nanograms (10 ng) of plasmid DNA was added to the reaction mixture for generating RCA product DNA in presence of 0.8 mM of random hexamers.

Preparation of template DNA: A plasmid DNA was first denatured by alkaline denaturation in the presence of EDTA. For denaturation, a volume containing about 22 µg of re-suspended plasmid DNA template was mixed with an equal volume on 0.4 N sodium hydroxide and 0.4 M EDTA in a tube. After incubating at room temperature for 5 minutes, 3 M acetic acid was added to the tube to have a final concentration of 0.4 M, followed by addition of ethanol to a final concentration of 75% of the total volume. The tube was then incubated in a dry ice-ethanol bath for 30 minutes. Precipitated plasmid DNA was collected by centrifugation at room temperature (30° C.) and greater than 20,000 times gravity for 30 minutes. The plasmid DNA pellet obtained after centrifugation was washed with about 500 µl of ice cold 70% (v/v) ethanol and re-centrifuged at the room temperature (30° C.) and greater than 20,000 times gravity for 15 minutes. After re-centrifugation, the denatured plasmid DNA was re-suspended in water and the concentration was determined by spectrophotometry. The denatured plasmid DNA was used on the same day for RCA reaction to produce RCA product DNA. For producing double stranded RCA (dsRCA) product, a non-denatured plasmid DNA template and smaller random hexamers were used.

Rolling-circle amplification (RCA): The amplification of the plasmid DNA template was performed using the decontaminated enzyme mix and the primer-nucleotide mix. For example, the polymerase solution containing 200 ng of Phi29 DNA polymerase was incubated with 0.1 unit of exonuclease III in 5 µL of 50 mM HEPES buffer (pH=8.0) containing 15 mM KCl, 20 mM $MgCl_2$, 0.01% Tween-20 and 1 mM TCEP. The incubation was performed either at 30° C. for about 60 min or at 4° C. for 12 h. The decontaminated Phi29 DNA polymerase solution was transferred to an ice-bath and then was used in the target RCA assay without prior inactivation of the exonuclease III. For rolling-circle amplification, the amplification reaction mixture comprised 40 µM primer, 400 µM dNTPs (400 µM each of dATP, dCTP, dGTP, dTTP); ~1-30 ng of circular DNA template (the plasmid DNA), 20 ng/µL of phi29 DNA polymerase, 50 mM HEPES (pH=8.0), 75 mM KCl, 20 mM $MgCl_2$, 0.01% (v/v) Tween-20, and 1 mM TCEP. At the end of the incubation, the Phi29 DNA polymerase in the reaction mixture was inactivated by heating the reaction mixture at 65° C. for 10 minutes. In some examples, thioated dATP was supplemented at a 1:1600 ratio (e.g., 0.01 mM alpha-S-dATP) or 125:1600 ratio relative to the total dNTP solution.

RCA reactions using pAcGFP1-Hyg-C1 plasmid, pCMV-AC-mKate2 plasmid, and plasmid RW218 were performed under two different test conditions, (i) using random hexamer primers and dNTPs, (ii) using random hexamer primers and dNTPs mixed with thioated dNTPs.

Example 2: To Confirm Inclusion of Phosphorothioated Nucleotide to a Double Stranded Concatemeric DNA on Rolling Circle Amplification by Determining Stability of the RCA Product DNA on Restriction Digestion In this example, the stability of the modified RCA product DNA (thioated) compared to unmodified RCA product DNA (non-thioated) and supercoiled plasmid DNA was determined. The inclusion of phosphorothioated nucleotide to double stranded concatemeric DNA, such as RCA product DNA, generally increases the stability of the DNA on exposure to restriction enzymes. The increased stability of the thioated DNA (RCA product) compared to the non-thioated DNA and plasmid DNA also confirms the successful inclusion of phosphorothioated nucleotide to the RCA product DNA.

The DNA was prepared either by purification of RW218 expression plasmid from *E. coli* as supercoiled plasmid DNA, or prepared by rolling circle amplification using either a standard RCA reaction or one in which alpha-phosphorothioated-dATP was added in a 1:1600 ratio compared to total dNTP in the amplification reaction. The plasmid DNA RW218 that encodes the hemagglutinin (HA) gene was employed as a negative control. The non-thioated RCA product DNA (RCA-RW218), and the thioated RCA product DNA (thio-RCA-RW218) were formed by using plasmid DNA encoding HA as a template. To determine the nuclease resistant property, 200 ng of different DNA samples, such as thioated RCA product DNA, non-thioated RCA product DNA and supercoiled plasmid DNA, were subjected to restriction digestion with HindIII in a 40 µl of reactions containing 50 mM NaCl, 10 mM Tris-HCl, pH8, 10 mM $MgCl_2$ and 80 units of HindIII. The reactions were incubated at 37° C. for one hour, then at 80° C. for 15 minutes to inactivate HindIII. 10 units of ExoI and ExoIII were added to 12 µl of aliquots of HindIII digested DNA as described above and then the reactions were incubated at 37° C. for 15 and 30 minutes, respectively. These three types of DNA (thio-RCA-RW218, RCA-RW218 and plasmid RW218) were digested using HindIII to generate a linear DNA fragment followed by restriction digestion with ExoI and ExoIII. Exo I and Exo III were added to the solution containing different DNA samples (such as thio-RCA-RW218, RCA-RW218 and RW218 plasmid) and HindIII, and incubated the samples at 37° C. for 0, 30 min or 60 min.

Figure 1:
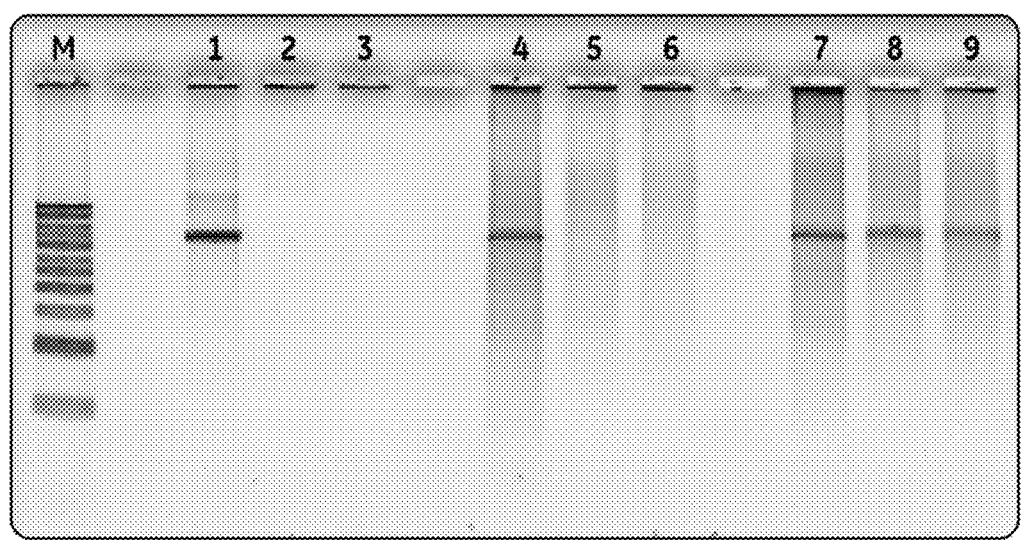
FIG. 1 is an image of agarose gel electrophoresis illustrating in vitro stability of a RCA product DNA comprising phosphorothioated nucleotides compared to super coiled plasmid DNA and a RCA product DNA devoid of phosphorothioated nucleotides.

Agarose gel electrophoresis of the samples of digestion product was performed, wherein the intensity of each of the electrophoresis bands was compared to those of standards having known concentration of DNA (DNA marker, denoted as M in FIG. 1). The samples of the digestion product were collected at 0 min (FIG. 1, lanes 1, 4, 7), 15 min (FIG. 1, lanes 2, 5, 8) and 30 min (FIG. 1, lanes 3, 6 and 9) and were subjected to agarose gel electrophoresis (FIG. 1). FIG. 1 illustrates the restriction digestion product of the supercoiled plasmid DNA (lanes 1-3), or RCA product DNA (lanes 4-6), and thioated RCA product DNA (lanes 7-9). FIG. 1 shows that the thioated RCA DNA (containing approximately 1 thioated base in 1600 total nucleotides) is resistant to degradation by the restriction digestion by double stranded DNA exonuclease and single stranded DNA exonuclease (see FIG. 1, lanes 8 and 9). This data further establishes the fact that the RCA product DNA gets thioated by adding thioated nucleotides during RCA reaction.

Example 3: In Vivo Stability of the Thioated RCA Product DNA and Expression of GFP Cell culture: The adherent cell line HEK293 was used for the following experiments to evaluate the persistence of expression from a RCA donor DNA with modified bases. On day 0, cells were plated in a cell culture medium-treated 96-well plate. The plating density for HEK293 cell line was 30,000 cells per well. The cells were allowed to settle for overnight at 37° C. in a 5% $CO_2$ incubator to induce attachment of the cells to the inner surface of the wells of the 96-well plate. On day 1, the cultured cells were used for cell transfection experiments. The transfection mixture was made, the media was aspirated off from the cells, and the transfection mixture was then added to the cells.

Cell Transfection with Lipofectamine 2000 for GFP expression: The RCA product DNA and the pAcGFP1-Hyg-C1 expression plasmid DNA (100 ng/µl) were prepared in 10 mM Tris, pH 8.0. 100 ng of RCA product DNA was added to a final volume of 25 µL in serum free medium (with no Penicillin, Streptomycin and L-glutamine) to form a DNA sample. 0.5 µL Lipofectamine 2000 was added to 24.5 µL serum free medium in a separate tube to form a Lipofectamine solution. 25 µL DNA sample from each tube was added to 25 µL of Lipofectamine solution, mixed gently to form a total volume of 50 µL transfection mixture, which was incubated at room temp for 20 minutes. 30,000 cells were plated per well in 100 µL complete medium. The entire 50 µL transfection mixture was added to the cells followed by incubation for overnight at 37° C., under 5% $CO_2$ environment. Next day, the medium was replaced with a fresh complete medium. The image was taken by using fluorescent microscope (IN Cell analyzer, GE Healthcare Life Sciences) at day 2, 5, 10, and 20 after transfection using supercoiled plasmid DNA (designated as GFP plasmid in FIG. 2), non-thioated RCA product DNA (GFP RCA in FIG. 2) and RCA product DNA with thioated ATP in concentration of 1:1600 (designated in FIG. 2 as GFP RCA-thioA (1:1600)) and 125:1600 (designated in FIG. 2 as GFP RCA-thioA (125:1600)).

Cell samples were analyzed using a FC500 (Beckman Coulter) flow cytometer. Cells were diluted in 200-400 µL of buffer depending on the total cell count in the sample. The cell concentration was optimized such that the concentration of cells was high enough to obtain adequate signal, at the same time the concentration was low enough to read within the accurate range of the flow cytometer. Flow cytometer highlighted all events that were deemed cells by removing all non-cell debris from the analysis. Further, all GFP positive cells from the total cell sample were parses out. Percent GFP cells was calculated from the total cell population. Intensity of GFP positive cells can be measured from the total cell population as well as the GFP positive cell sub-population. As the RCA product DNA (both thioated and non-thioated) and the plasmid DNA containing a GFP insert were transfected into the cells, the percentage of GFP positive cells were quantified to estimate the in vivo stability of the plasmid DNA and the RCA product DNA. FIG. 2 represents normalized (with respect to the signal on day 1)

percent of GFP expression. The percent GFP expression is the percentage of cells that were positive for GFP expression within the total cell population.

After transfection with supercoiled plasmid DNA, RCA product DNA or thioated RCA product DNA, HEK293 cells were harvested for flow cytometry analysis. The average relative fluorescence unit (RFU) of GFP signal remaining after the indicated days, was normalized to day 1 and the results are depicted in FIG. 2. FIG. 2. indicates that both non-thioated RCA product DNA and thioated RCA product DNA may remain intact and active for a greater duration in vivo compared with supercoiled plasmid DNA. FIG. 2 also illustrates that the stability of the thioated RCA product DNA is more than the non-thioated RCA product DNA or supercoiled plasmid DNA. The thioated RCA product DNA having thioA in ratio 125:1600 showed even better stability than the thioated RCA product DNA having thio A in a ratio 1:1600 compared to total dNTPs.

Example 4: In Vivo Stability of the Thioated RCA Product DNA and Expression of RFP Cell Transfection with Lipofectamine 2000 for RFP expression: The RCA product DNA and the mKate2-RFP expression plasmid DNA (100 ng/µl) were prepared in 10 mM Tris, pH 8.0. 600 ng of RCA product DNA was added to a final volume of 25 µL in serum free medium (with no Penicillin, Streptomycin and L-glutamine) to form a DNA sample. 2 µL Lipofectamine 2000 was added to 23 µL serum free medium in a separate tube to form a Lipofectamine solution. 25 µL DNA sample from each tube was added to 25 µL of Lipofectamine solution, mixed gently to form a total volume of 50 µL transfection mixture, which was incubated at room temp for 20 minutes. 100,000 cells were plated per well in 500 µL complete medium in a 24-well plate in the evening before the day of transfection. Next day, the medium was replaced with 450 uL of serum free medium (Penicillin, Streptomycin and L-glutamine). The entire 50 µL transfection mixture was added to the cells followed by incubation for overnight at 37° C., under 5% $CO_2$ environment. Next day, the medium was replaced with a fresh complete medium. The image was taken by using fluorescent microscope (IN Cell analyzer, GE Healthcare Life Sciences) at day 2 and 9 for example using RCA product DNA with thioated CTP (designated in FIG. 3 as RFP RCA-thioC (1:1600) and RFP RCA-thioC (125:1600)), RCA product DNA with thioated TTP (designated in FIG. 3 as RFP RCA-thioT (1:1600) and RFP RCA-thioT (125: 1600)). For another example, the image was taken by using the same fluorescent microscope at days 2, 9, 14, and 21 using RCA product DNA with thioated ATP (designated in FIG. 4 as RFP RCA-thioA (1:1600) and RFP RCA-thioA (125:1600)), RCA product DNA with thioated GTP (designated in FIG. 4 as RFP RCA-thioG (1:1600) and RFP RCA-thioG (125:1600)) after transfection. The samples were analyzed by flow cytometry.

As both thioated and non-thioated RCA product DNA and the plasmid DNA containing a RFP insert was transfected into the cells, the percentage of RFP positive cells were quantified to estimate the in vivo stability of the plasmid DNA and the RCA product DNA. FIGS. 3 and 4 represent normalized average relative fluorescence unit (RFU) of cells for RFP expression, wherein the measured and normalized average percent RFU of RFP is the relative fluorescence unit of RFP acquired by total number of cells that were positive for RFP expression within the total cell population.

Cell samples were analyzed using a FC500 (Beckman Coulter) flow cytometer as described in Example 3. After transfection with supercoiled plasmid DNA, non-thioated RCA product DNA or thioated RCA product DNA, HEK293 cells were harvested for flow cytometry analysis. The average percent RFU of RFP signal remaining after the indicated days, was normalized to day 1 and the results are depicted in FIGS. 3 and 4.

The foregoing examples are illustrative of some features of the invention, and are selected embodiments from a manifold of all possible embodiments. The invention may be embodied in other specific forms without departing from the spirit or essential characteristics thereof. While only certain features of the invention have been illustrated, and described herein, one skilled in the art, given the benefit of this disclosure, will be able to make modifications/changes to optimize the parameters. The foregoing embodiments are therefore to be considered in all respects as illustrative rather than limiting on the invention described herein.

Where necessary, ranges have been supplied, and those ranges are inclusive of all sub-ranges there between.

The invention claimed is:

1. A method for in vivo RNA or protein expression, the method comprising:
   introducing a double-stranded concatemeric DNA into a eukaryotic cell to generate a desired RNA or protein, wherein the double-stranded concatemeric DNA comprises a plurality of tandem repeat sequences, and wherein each of the plurality of tandem repeat sequences comprises an expression sequence,
   wherein the double-stranded concatemeric DNA comprises one or more phosphorothioated nucleotides; and wherein a ratio of phosphorothioated nucleotides to total nucleotides in the double-stranded concatemeric DNA is at least 1:1600.

2. The method of claim 1, wherein the double-stranded concatemeric DNA is a rolling circle amplification (RCA) product DNA.

3. The method of claim 1, wherein the ratio of phosphorothioated nucleotides to total nucleotides in the double-stranded concatemeric DNA is in a range of 1:1600 to 125:1600.

4. The method of claim 1, wherein the ratio of phosphorothioated nucleotides to total nucleotides in the double-stranded concatemeric DNA is in a range of 50:1600 to 125:1600.

5. The method of claim 1, wherein the ratio of phosphorothioated nucleotides to total nucleotides in the double-stranded concatemeric DNA is in a range of 75:1600 to 125:1600.

6. The method of claim 1, wherein the ratio of phosphorothioated nucleotides to total nucleotides in the double-stranded concatemeric DNA is 125:1600.

7. The method of claim 1, wherein the double-stranded concatemeric DNA is an unprocessed or a processed RCA product DNA.

8. The method of claim 1, wherein the expression sequence comprises a coding sequence, a non-coding sequence, or a combination thereof.

9. The method of claim 8, wherein the coding sequence comprises a promoter, an open reading frame, and optionally a cap-independent translation element (CITE).

10. The method of claim 9, wherein the cap-independent translation element (CITE) comprises an internal ribosome entry site (IRES), a translation enhancing element (TEE), or a combination thereof.

11. The method of claim 9, wherein the open reading frame comprises a codon-optimized sequence for enhancing translation.

12. The method of claim 9, wherein the open reading frame comprises a tag sequence for purification of the desired protein, an amino-terminal peptide fusion sequence derived from an IRES for enhanced ribosome recognition, or a combination thereof.

13. The method of claim 8, wherein the non-coding sequence comprises a promoter and a transcription termination sequence.

14. The method of claim 8, wherein the non-coding sequence comprises a sequence for antisense RNA, a short interfering RNA (siRNA), a short hairpin RNA (shRNA), a microRNA (miRNA), a microRNA mimic, a transfer RNA (tRNA), a ribosomal RNA (rRNA), CRISPR RNAs, or combinations thereof.

15. The method of claim 1, wherein the expression sequence is a minimalistic expression sequence that is devoid of any extraneous sequences that are required for propagation of a plasmid in a host cell.

16. The method of claim 1, wherein the expression sequence further comprises a polyA sequence, a transcriptional termination sequence, an insulator sequence, or a combination thereof.

17. The method of claim 1, wherein the double-stranded concatemeric DNA further comprises an inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide, or a combination thereof.

18. The method of claim 1, wherein the double-stranded concatemeric DNA is delivered to a eukaryotic cell by electroporation, sonoporation, impalefection, transduction, optical transfection, magnetofection, nucleofection, hydrodynamic delivery, heat shock-mediated gene delivery, nanoparticle mediated gene-gun delivery, calcium phosphate-mediated delivery, cationic polymer-mediated delivery, or liposome-mediated delivery.

19. The method of claim 1, wherein the double-stranded concatemeric DNA is an RCA product DNA produced using a primer comprising an inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide, or a combination thereof.

20. A eukaryotic cell comprising:
an exogeneous, double-stranded concatemeric DNA comprising a plurality of tandem repeat sequences;
wherein each of the plurality of tandem repeat sequences comprises a phosphorothioated nucleotide, and
wherein a ratio of phosphorothioated nucleotides to total nucleotides is at least 1:1600.

21. The eukaryotic cell of claim 20, wherein the exogeneous, double-stranded concatemeric DNA is an unprocessed or a processed RCA product DNA.

22. The eukaryotic cell of claim 20, wherein the eukaryotic cell comprises a protozoa, a yeast cell, an insect cell, a plant cell, or a mammalian cell.

* * * * *